(12) United States Patent
Samain et al.

(10) Patent No.: US 11,191,340 B2
(45) Date of Patent: Dec. 7, 2021

(54) TRANSFER DEVICE FOR MAKING UP KERATIN MATERIALS

(71) Applicant: L'OREAL, Paris (FR)

(72) Inventors: Henri Samain, Bievres (FR); Franck Giron, Lagny sur Marne (FR); Chrystéle Gevrey, Sucy en Brie (FR)

(73) Assignee: L'OREAL, Paris (FR)

( * ) Notice: Subject to any disclaimer, the term of this patent is extended or adjusted under 35 U.S.C. 154(b) by 90 days.

(21) Appl. No.: 15/108,295

(22) PCT Filed: Dec. 19, 2014

(86) PCT No.: PCT/IB2014/067135
§ 371 (c)(1),
(2) Date: Jun. 25, 2016

(87) PCT Pub. No.: WO2015/097617
PCT Pub. Date: Jul. 2, 2015

(65) Prior Publication Data
US 2016/0316890 A1 Nov. 3, 2016

(30) Foreign Application Priority Data
Dec. 27, 2013 (FR) ..................................... 1363640

(51) Int. Cl.
*A45D 40/30* (2006.01)
*A45D 33/38* (2006.01)
(Continued)

(52) U.S. Cl.
CPC ............. *A45D 40/30* (2013.01); *A45D 33/38* (2013.01); *A45D 40/00* (2013.01); *A61K 8/0204* (2013.01);
(Continued)

(58) Field of Classification Search
CPC .... A45D 40/30; A45D 40/0087; A45D 33/38; A45D 2200/1027; A61K 8/0208; A61K 8/0212; A61K 8/022; A61Q 1/12
(Continued)

(56) References Cited

U.S. PATENT DOCUMENTS 2,746,460 A   5/1956   Jellinek
4,137,180 A   1/1979   Naik et al.
(Continued)

FOREIGN PATENT DOCUMENTS

CN   1476319 A   2/2004
CN   1519278 A   8/2004
(Continued)

OTHER PUBLICATIONS

International Search Report for PCT/IB2014/067135 dated Mar. 11, 2015 (3 pages).
(Continued)

*Primary Examiner* — Edward Moran
(74) *Attorney, Agent, or Firm* — Shumaker, Loop & Kendrick, LLP

(57) ABSTRACT

Process for making up an area of human keratin materials using a makeup device having a transfer surface and a coat of at least one cosmetic colouring ink borne by the transfer surface and obtained by printing using at least one digital printer, the colouring ink being intended to be applied to the keratin materials. The process includes the following steps: forming a base coating by applying at least one cosmetic composition comprising an oil onto the area of the keratin materials to be made up, and producing a pattern on the area of the keratin materials by placing the coat of cosmetic ink in contact with the base coating present on the area to be made up so as to transfer the coat of cosmetic ink onto the keratin materials.

8 Claims, 1 Drawing Sheet

(51) Int. Cl.
| | | |
|---|---|---|
| A45D 40/00 | (2006.01) | |
| A61K 8/92 | (2006.01) | |
| A61Q 1/02 | (2006.01) | |
| A61K 8/02 | (2006.01) | |
| A61K 8/06 | (2006.01) | |
| A61Q 1/04 | (2006.01) | |
| B44C 1/17 | (2006.01) | |

(52) U.S. Cl.
CPC .............. *A61K 8/0208* (2013.01); *A61K 8/06* (2013.01); *A61K 8/922* (2013.01); *A61Q 1/02* (2013.01); *A61Q 1/025* (2013.01); *A61Q 1/04* (2013.01); *B44C 1/1704* (2013.01); *A45D 2200/1027* (2013.01); *A45D 2200/1036* (2013.01); *A61K 2800/87* (2013.01)

(58) Field of Classification Search
USPC .......... 132/200, 319, 320; 604/303; 424/401
See application file for complete search history.

(56) References Cited

U.S. PATENT DOCUMENTS

| | | | |
|---|---|---|---|
| 4,804,719 A | 2/1989 | Weaver et al. | |
| 4,874,554 A | 10/1989 | Lange et al. | |
| 4,903,840 A | 2/1990 | So | |
| 4,925,667 A | 5/1990 | Fellows et al. | |
| 4,936,325 A * | 6/1990 | Davis | A45D 40/30 132/216 |
| 4,999,418 A | 3/1991 | Krutak et al. | |
| 5,030,708 A | 7/1991 | Krutak et al. | |
| 5,032,670 A | 7/1991 | Parham et al. | |
| 5,043,376 A | 8/1991 | Sharma et al. | |
| 5,047,084 A | 9/1991 | Miller et al. | |
| 5,078,160 A | 1/1992 | Carbonnier | |
| 5,102,980 A | 4/1992 | Krutak et al. | |
| 5,104,913 A | 4/1992 | Sharma et al. | |
| 5,106,942 A | 4/1992 | Krutak et al. | |
| 5,194,463 A | 3/1993 | Krutak et al. | |
| 5,281,659 A | 1/1994 | Weaver et al. | |
| 5,396,913 A * | 3/1995 | Wallschlaeger | A45D 40/0087 132/320 |
| 5,421,765 A | 6/1995 | Lehmann et al. | |
| 5,913,315 A | 6/1999 | Todd | |
| 5,958,560 A | 9/1999 | Ewan | |
| 5,997,134 A | 12/1999 | Hotomi et al. | |
| 5,997,136 A | 12/1999 | Fujisawa et al. | |
| 6,013,248 A * | 1/2000 | Luebbe | A61K 8/042 424/400 |
| 6,106,852 A | 8/2000 | Vineberg | |
| 6,168,656 B1 | 1/2001 | Schulz et al. | |
| 6,190,730 B1 | 2/2001 | Matsos et al. | |
| 6,299,967 B1 | 10/2001 | Collins et al. | |
| 6,312,124 B1 | 11/2001 | Desormeaux | |
| 6,342,094 B1 | 1/2002 | Kabalnov | |
| 6,367,484 B1 | 4/2002 | Ramin et al. | |
| 6,428,164 B1 | 8/2002 | Missell et al. | |
| 6,543,893 B2 | 4/2003 | Desormeaux | |
| 6,622,733 B2 | 9/2003 | Saksa | |
| 6,626,183 B1 | 9/2003 | Pietrocola et al. | |
| 7,241,503 B2 | 7/2007 | Noguchi | |
| 7,648,364 B2 | 1/2010 | Dauga et al. | |
| 8,007,062 B2 | 8/2011 | Edgar et al. | |
| 8,083,422 B1 | 12/2011 | Simmons | |
| 8,545,613 B2 | 10/2013 | Blette | |
| 8,695,610 B2 | 4/2014 | Samain | |
| 9,616,668 B1 | 4/2017 | Rabe | |
| 2002/0020422 A1* | 2/2002 | Iosilevich | A45D 40/30 132/200 |
| 2002/0035182 A1 | 3/2002 | L'Alloret et al. | |
| 2002/0061321 A1 | 5/2002 | Bara | |
| 2002/0110672 A1* | 8/2002 | Muratore-Pallatino | B32B 7/06 428/195.1 |
| 2002/0155069 A1 | 10/2002 | Pruche | |
| 2002/0164295 A1* | 11/2002 | Scavone | A61K 8/11 424/65 |
| 2003/0053976 A1 | 3/2003 | Tournilhac et al. | |
| 2004/0057742 A1 | 3/2004 | Richtsmeier | |
| 2004/0078278 A1 | 4/2004 | Dauga | |
| 2004/0241423 A1 | 12/2004 | Ramin et al. | |
| 2004/0246327 A1 | 12/2004 | Elzi | |
| 2005/0148908 A1 | 7/2005 | Stover | |
| 2006/0093943 A1 | 5/2006 | Shu et al. | |
| 2006/0098076 A1 | 5/2006 | Liang | |
| 2006/0150994 A1 | 7/2006 | Pilmanis | |
| 2007/0144634 A1 | 6/2007 | Hitchcock | |
| 2008/0031836 A1 | 2/2008 | Ilekti | |
| 2008/0053476 A1 | 3/2008 | LaHood et al. | |
| 2008/0152681 A1* | 6/2008 | Brown | A61K 8/042 424/401 |
| 2008/0176160 A1 | 7/2008 | Deprez et al. | |
| 2009/0325221 A1* | 12/2009 | Long | A61B 5/14539 435/34 |
| 2010/0031834 A1 | 2/2010 | Morgavi et al. | |
| 2010/0068247 A1 | 3/2010 | Mou et al. | |
| 2010/0086693 A1 | 4/2010 | Yamada et al. | |
| 2011/0020023 A1 | 1/2011 | Hirai | |
| 2011/0025040 A1 | 2/2011 | Dominguez | |
| 2011/0123703 A1 | 5/2011 | Mohammadi et al. | |
| 2011/0141188 A1 | 6/2011 | Morita | |
| 2011/0159463 A1 | 6/2011 | Samain | |
| 2011/0164263 A1 | 7/2011 | Samain et al. | |
| 2011/0268873 A1* | 11/2011 | Blette | A61K 8/345 427/147 |
| 2012/0027423 A1 | 2/2012 | Kawai | |
| 2012/0027443 A1 | 2/2012 | Kawai | |
| 2012/0029417 A1 | 2/2012 | Samain et al. | |
| 2012/0064011 A1 | 3/2012 | Schumann | |
| 2012/0192884 A1 | 8/2012 | Nasu et al. | |
| 2012/0244316 A1* | 9/2012 | Dobler | A61K 8/37 428/141 |
| 2012/0244465 A1 | 9/2012 | Kobayashi | |
| 2012/0307304 A1 | 12/2012 | Moreno | |
| 2013/0216295 A1 | 8/2013 | Wong | |
| 2014/0233967 A1 | 8/2014 | Suzuki | |
| 2015/0053759 A1 | 2/2015 | Cahill et al. | |
| 2015/0150767 A1 | 6/2015 | Klug et al. | |
| 2016/0000208 A1 | 1/2016 | Wong | |
| 2016/0103962 A1 | 4/2016 | Costantino et al. | |
| 2016/0316891 A1 | 11/2016 | Samain | |
| 2016/0316892 A1 | 11/2016 | Giron | |
| 2016/0317403 A1 | 11/2016 | Giron | |
| 2016/0324298 A1 | 11/2016 | Samain | |
| 2016/0324299 A1 | 11/2016 | Samain | |
| 2019/0133300 A1* | 5/2019 | Hedglin | B44C 1/105 |

FOREIGN PATENT DOCUMENTS

| | | |
|---|---|---|
| CN | 101010064 A | 8/2007 |
| CN | 101056605 A | 10/2007 |
| CN | 101686927 A | 3/2010 |
| CN | 101980694 A | 2/2011 |
| CN | 102490540 A | 6/2012 |
| DE | 102005050123 A1 | 4/2007 |
| EP | 705593 A1 | 4/1996 |
| EP | 0728460 A1 | 8/1996 |
| EP | 0749746 A1 | 12/1996 |
| EP | 0749747 A1 | 12/1996 |
| EP | 780114 A1 | 6/1997 |
| EP | 0923928 A1 | 6/1999 |
| EP | 0930060 A1 | 7/1999 |
| EP | 0938887 A1 | 9/1999 |
| EP | 1000607 A1 | 5/2000 |
| EP | 1048282 A1 | 11/2000 |
| EP | 1059047 A1 | 12/2000 |
| EP | 1304056 A2 | 4/2003 |
| EP | 1925278 A1 | 5/2008 |
| EP | 2090935 A1 | 8/2009 |
| FR | 2232303 A1 | 1/1975 |
| FR | 2759941 A1 | 8/1998 |
| FR | 2792192 A1 | 10/2000 |

(56) References Cited

FOREIGN PATENT DOCUMENTS

| | | |
|---|---|---|
| FR | 2858226 A1 | 2/2005 |
| FR | 2900594 A | 8/2007 |
| FR | 2905630 A1 | 3/2008 |
| FR | 2909844 A1 | 6/2008 |
| FR | 2939033 A1 | 6/2010 |
| JP | S62180000 A | 8/1987 |
| JP | S63-188616 A | 8/1988 |
| JP | H-2503065 A | 9/1990 |
| JP | H04-208997 A | 7/1992 |
| JP | H11-007203 A | 1/1999 |
| JP | H11-169231 A | 6/1999 |
| JP | H11169231 A | 6/1999 |
| JP | H-11169231 A | 6/1999 |
| JP | H11-346828 A | 12/1999 |
| JP | 2001-245945 A | 9/2001 |
| JP | 2001278739 A | 10/2001 |
| JP | 3266197 B2 | 1/2002 |
| JP | 2002-058528 A | 2/2002 |
| JP | 2002068935 A | 3/2002 |
| JP | 2002-148998 A | 5/2002 |
| JP | 2003006452 A | 1/2003 |
| JP | 2004501177 A | 1/2004 |
| JP | 2004262913 A | 9/2004 |
| JP | 2005040356 A | 2/2005 |
| JP | 2005-088434 A | 4/2005 |
| JP | 2007204487 A | 8/2007 |
| JP | 2008-127388 A | 6/2008 |
| JP | 2010505843 A | 2/2010 |
| JP | 2010-186133 A | 8/2010 |
| JP | 2012-002869 A | 1/2012 |
| JP | 2012502908 A | 2/2012 |
| JP | 2012072081 A | 4/2012 |
| JP | 2012-518457 A | 8/2012 |
| JP | 2012518457 A | 8/2012 |
| JP | 2012-520837 A | 9/2012 |
| JP | 2012249849 A | 12/2012 |
| JP | 2013-031504 A | 2/2013 |
| JP | 2013137758 A | 7/2013 |
| JP | 2013532003 A | 8/2013 |
| JP | 2013-252709 A | 12/2013 |
| WO | 1992007913 A1 | 5/1992 |
| WO | 02/36083 A1 | 5/2002 |
| WO | 03033270 A1 | 4/2003 |
| WO | 2006/128737 A1 | 12/2006 |
| WO | 2006128737 A1 | 12/2006 |
| WO | 2007/134171 A1 | 11/2007 |
| WO | 2010/004526 A1 | 1/2010 |
| WO | 2010004526 A1 | 1/2010 |
| WO | 2010004531 A1 | 1/2010 |
| WO | 2010/095118 A | 8/2010 |
| WO | 2010/105842 A2 | 9/2010 |
| WO | 2012081065 A1 | 6/2012 |
| WO | 2013093889 A2 | 6/2013 |
| WO | 2013126513 A1 | 8/2013 |
| WO | 2013178701 A2 | 12/2013 |

OTHER PUBLICATIONS

Written Opinion for PCT/IB2014/067135 (5 pages).
Dyno Pretty Pup: "Dyno Pretty Pup Beauty Diary: LA Colors 30 Eye Design Paletts—Review." Mar. 16, 2012 (4 pages).
Restriction and Election of Species Requirement in U.S. Appl. No. 15/108,292 dated Mar. 1, 2017 (8 pages).
Non-Final Office Action in U.S. Appl. No. 15/108,076 dated Mar. 16, 2017 (12 pages).
"Papilio Laser Printable Temporary Tattoo Paper" (http://www.papilio.com/laser temporary tattoo paper.html), Dec. 14, 2013 (3 pages).
"Cheap laser printer paper for toner transfer?" (http://www.fountainpennetwork.com/forum/topic/41250-cheap-laser-printer-paper-for-toner-transfer/), Oct. 2, 2007 (11 pages).
Non-Final Office Action for U.S. Appl. No. 15/108,292 dated Jul. 7, 2017.
Final Rejection for U.S. Appl. No. 15/108,076 dated Aug. 21, 2017.
Canon, fix your own printer, https://www.fixyourownprinter.com/posts/66407 (dated: Mar. 17, 2010) (1 page).
Restriction Requirement for U.S. Appl. No. 15/108,303 dated Sep. 6, 2017 (7 pages).
Non-Final Office Action in U.S. Appl. No. 15/108,192 dated Oct. 6, 2017 (6 pages).
First Office Action for CN Pat. Appln. No. 201480076509.2 with English Translation dated Oct. 30, 2017, 9 pages.
Final Rejection for U.S. Appl. No. 16/108,292 dated Jan. 30, 2018, 21 pages.
Apr. 12, 2018 Office Action issued in U.S. Appl. No. 15/108,303.
Office Action dated May 18, 2018 for Chinese Patent Application No. 2014800713416 (22 pages).
Office Action dated Apr. 23, 2018 in European Patent Application No. 14 833 256.2.
International Search Report for PCT/IB2014/067130 dated Mar. 11, 2015 (5 pages).
International Search Report for PCT/IB2014/067132 dated Apr. 28, 2015 (4 pages).
International Search Report for PCT/IB2014/067133 dated Mar. 11, 2015 (5 pages).
International Search Report for PCT/IB2014/067134 dated Apr. 24, 2015 (4 pages).
International Search Report for PCT/IB2014/067136 dated Jul. 7, 2015 (5 pages).
International Search Report for PCT/IB2014/067138 dated Mar. 11, 2015 (3 pages).
Office Action issued in Chinese Application No. 201480071272.9 dated Jul. 2, 2018 (14 pp).
Office Action issued in U.S. Appl. No. 15/108,151 dated Aug. 7, 2018 (60 pp).
Office Action for JP App. No. 2016-543027 dated Dec. 21, 2018 with English Translation (13 pages).
Office Action for JP App. No. 2016-543057 dated Dec. 17, 2018 with English Translation (14 pages).
Office Action for JP App. No. 2016-543072 dated Dec. 17, 2018 with English Translation(7 pages).
Office Action for JP App. No. 2016-543056 dated Dec. 17, 2018 with English Translation (7 pages).
Office Action dated Jul. 2, 2018 issued in Japanese Patent Application No. 2016-543073 (17pp).
Office Action dated Jun. 5, 2018 issued in Chinese Patent Application No. 201480074439.7 (16 pp).
Office Action dated Sep. 10, 2018 in Japanese Patent Application No. 2016-542897 (7 pages).
Office Action dated Sep. 27, 2018 in U.S. Appl. No. 15/108,292 (16 pages).
Pubchem; castor oil—https://pubchem.ncbi.nlm.nih.gov/compound/castor_oil#section=Top; 1 page; 2010.
Chinese Office Action dated Dec. 5, 2018 in Chinese Application No. 201480071307.9 (8 pages).
Japanese Office Action dated Nov. 19, 2018 for Japanese Application No. 2016-542996 (32 pages).
LA Colors 30 Eye Design Palettes—Review, Dyno Pretty Pup, http://dynopupbeauty.blogspot.nl/2012/03/la-colors-30-eye-design-palettes-review.html, Mar. 16, 2012 (5 pages).
Notice of Allowance dated Nov. 13, 2018 issued in U.S. Appl. No. 15/108,303 (27 pages).
Final Rejection for U.S. Appl. No. 15/108,151 dated May 20, 2019 (11 pages).
Non-Final Office Action for U.S. Appl. No. 15/108,305 dated May 15, 2019 (17 pages).
Non-Final Office Action for U.S. Appl. No. 15/108,294 dated Mar. 4, 2019 (11 pgs.).
Non-Final Office Action for U.S. Appl. No. 15/108,302 dated Feb. 8, 2019 (7 pages).
Restriction Requirement for U.S. Appl. No. 15/108,305 dated Jan. 31, 2019 (8 pages).
English Translation of JP Office Action for JP Pat. App. No. 2016-542995 drafted Jan. 16, 2019 and dated Jan. 21, 2019 (3 pages).

(56) References Cited

OTHER PUBLICATIONS

Final Rejection for U.S. Appl. No. 15/108,292 dated Apr. 26, 2019 (7 pages).
Final Rejection for U.S. Appl. No. 15/108,302 dated Jul. 2, 2019 (7 pages).
Notice of Allowance for U.S. Appl. No. 15/108,294 dated Jul. 25, 2019 (9 pages).
Japanese Office Action for JP Pat. Appln. No. 2016-543057 dated Aug. 26, 2019 (8 pages).
Notice of Allowance for U.S. Appl. No. 15/108,292 dated Aug. 29, 2019 (16 pages).
Japanese Office Action for JP Pat. Appln. No. 2016-543056 dated Aug. 26, 2019 (8 pages).
Japanese Office Action for JP Pat. Appln. No. 2016-542996 dated Sep. 2, 2019 (14 pages).
Japanese Office Action for JP Pat. Appln. No. 2016-542897, dated Sep. 17, 2019 (10 pages).
Japanese Office Action for JP Patent App. No. 2016-543072 dated Mar. 12, 2020 with English translation (7 pages).
Examiner's Answer in response to Appeal Brief filed Dec. 4, 2019 for U.S. Appl. No. 15/108,302, dated Feb. 4, 2020 (7 pages).
Final Rejection for U.S. Appl. No. 15/108,305, dated Mar. 3, 2020 (24 pages).
Non-Final Office Action for U.S. Appl. No. 15/108,151 dated Feb. 25, 2021 (8 pages).
Office Action for Korean Patent App. No. 10-2016-7020078 dated Jan. 27, 2021 with English Translation (14 pages).
Non-Final Office Action for U.S. Appl. No. 15/108,305, dated Jan. 6, 2021 (14 pgs.).
Restriction Requirement for U.S. Appl. No. 16/694,035, dated Jan. 12, 2021 (8 pgs.).
Advisory Action for U.S. Appl. No. 15/108,151, dated Jan. 8, 2021 (3 pgs.).
Patent Board Decision—Examiner Affirmed for U.S. Appl. No. 15/108,302, dated Jan. 8, 2021 (10 pgs.).
Final Rejection for U.S. Appl. No. 15/108,305 dated Jun. 15, 2021 (15 pages).
Japanese Office Action for 2019-127617 dated Jun. 22, 2020 with English Translation (9 pages).
Korean Office Action for KR Pat. Appln. No. 10-2016-7020687, dated Feb. 25, 2021 with English Translation (22 pages).
Non-Final Office Action for U.S. Appl. No. 15/108,151 dated Jul. 20, 2020 (10 pages).
Non-Final Office Action for U.S. Appl. No. 15/108,302 dated Apr. 22, 2021 (10 pages).
Non-Final Office Action for U.S. Appl. No. 16/694,035 dated May 10, 2021 (7 pages).
Final Rejection for U.S. Appl. No. 15/108,151 dated Oct. 23, 2021 (8 pages).
Notice of Allowance for U.S. Appl. No. 15/108,302, dated Aug. 23, 2021 (9 pages).
European Office Action for EP Pat. Appln. No. 14833254.7 dated Aug. 30, 2021 (5 pages).
Corrected Notice of Allowance for U.S. Appl. No. 15/108,302 dated Sep. 8, 2021 (2 pages).
Non-Final Office Action for U.S. Appl. No. 15/108,151 dated Sep. 15, 2021 (10 pages).
Japanese Office Action for JP Pat. Appln. No. 2019-127617, drafted Aug. 12, 2021 and dated Sep. 6, 2021 with English Translation (11 pages).
Notice of Allowance for U.S. Appl. No. 15/108,305, dated Sep. 30, 2021 (13 pages).
Corrected Notice of Allowability for U.S. Appl. No. 16/694,035, dated Sep. 29, 2021 (2 pages).
Corrected Notice of Allowability for U.S. Appl. No. 15/108,302, dated Sep. 14, 2021 (2 pages).
Final Rejection issued for U.S. Appl. No. 16/694,035, dated Oct. 1, 2021 (11 pages).

\* cited by examiner

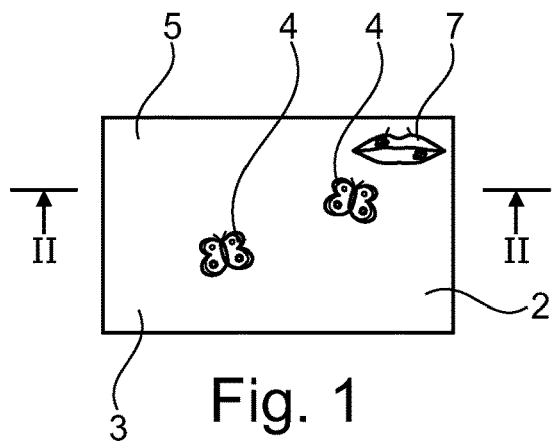
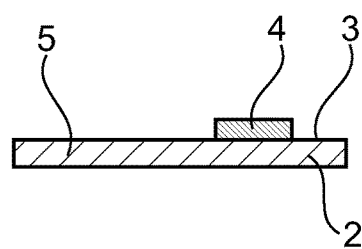
Fig. 1　　　　　Fig. 2
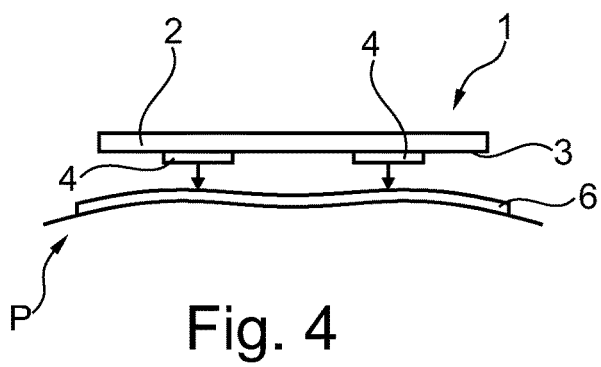
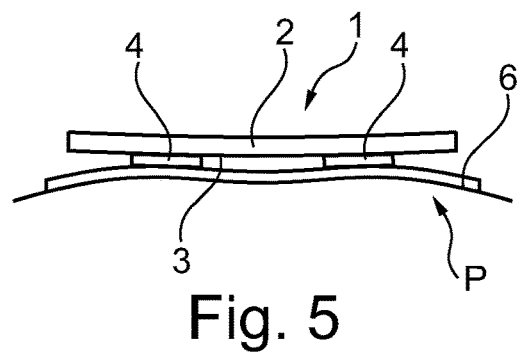
Fig. 4　　　　　Fig. 5
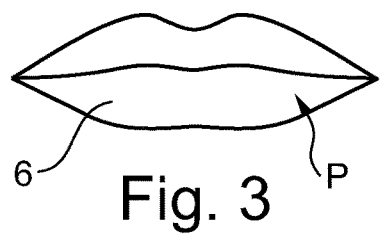
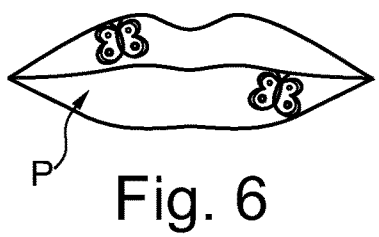
Fig. 3　　　　　Fig. 6
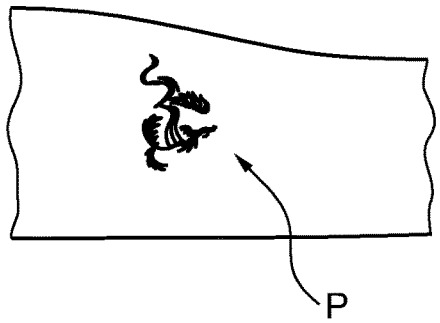
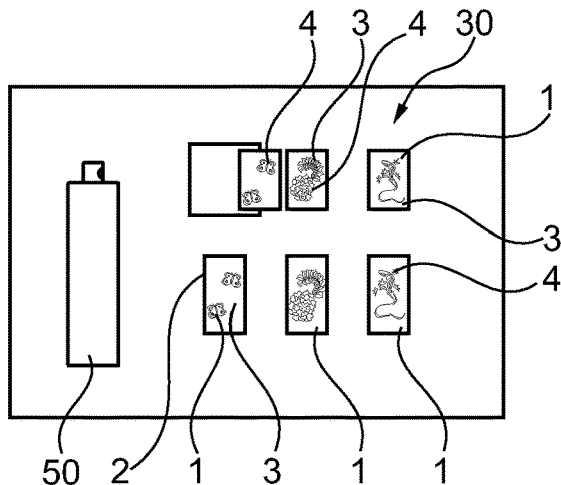
Fig. 7　　　　　Fig. 8

TRANSFER DEVICE FOR MAKING UP KERATIN MATERIALS

The present invention relates to makeup application by transfer.

BACKGROUND

The purpose of making up keratin materials is to make these areas beautiful.

There is a need to cover keratin materials, especially the skin and the lips, with precise coatings, such as patterns at the millimeter scale.

However, no practical and efficient method exists, Drawing a pattern takes a longtime to do and requires the intervention of a professional makeup artist. Methods using a patch or a decal transfer are disappointing, since the number of patterns is limited and it is difficult to avoid folds in the support bearing the pattern. This technique is, in particular, unsuitable for the face. On account of the movements of the facial skin, the support becomes cracked, thus giving a degraded and unaesthetic visual result.

There is a need to have available makeup patterns intended to cover a small area or indeed the entire area of the face or the lips.

There is a need to propose to each user a wide variety of patterns, colours, shapes and distributions, or even to propose to the user to define his patterns, so as best to satisfy his particular request, without the need to have a large number of references at hand.

Moreover, if the area to be made up has imperfections such as marks, microreliefs, wrinkles or fine lines, the makeup pattern has a less aesthetic result, not giving it a sharp, clean appearance.

There is a need for a makeup that is suited to the particular characteristics of the area of keratin materials to be treated. Thus, the makeup must occasionally be produced using a very thin coat of cosmetic ink to be comfortable for the user to wear, for example in the case of lip makeup.

There is a need to prepare the area to be made up so that the transfer keeps its precision intact and to have a beautiful, sharp and precise appearance.

The present invention is directed towards meeting all or some of these needs.

SUMMARY

According to a first aspect, the present invention relates to a process for making up an area of human keratin materials using a makeup device having a transfer surface and a coat of at least one cosmetic colouring ink borne by the transfer surface and Obtained by printing using at least one digital printer, the colouring ink being intended to be applied to the keratin materials.
the process comprising the following steps:
  forming a base coating by applying to the areas of the keratin materials to be made up at least one cosmetic composition comprising an oil,
  producing a pattern on the area of the keratin materials by placing the coat of cosmetic ink in contact with the base coating present on the area to be made up so as to transfer the coat of cosmetic ink onto the keratin materials.

The process may also comprise a step consisting in moving the transfer surface away from the area of the human keratin materials after the coat of ink has been transferred.

The makeup area may be an area of skin, especially of e face, the scalp or the lips.

By means of the invention, the user can decorate and/or treat the skin or the lips uniformly or with patterns.

The use of a coat of cosmetic ink obtained by printing using a printer advantageously makes it possible, when compared with standard makeup applications, to obtain a complex and customizable makeup result. The use of a base coating makes it possible to offer a practical method, which can be used in a few minutes for preparing the area to be made up. This preliminary step facilitates the production, by transfer of cosmetic ink, of precise patterns, especially on facial skin or the lips. The invention makes it possible, after transferring, for the pattern to keep its precision intact. The base coating may also facilitate the transfer of the ink.

The use of a base coating on the area to be made up prior to transferring the cosmetic ink may smooth out the area to be made up so as to improve its visual appearance.

The presence of the base coating also improves the visual rendering of the patterns, over the entire made-up area, without allowing skin defects to show through.

The process according to the invention makes it possible to cover small areas or the entire area of the face or of the lips.

The process according to the invention is compatible with the usual treatments for covering keratin materials.

The ink borne by the transfer surface comprises a dyestuff.

The transfer surface is, for example, an outer surface of a substrate.

Base Coating

The base coating may be prepared by applying one or more coats, each of identical or different composition.

The base coating may be colourless or coloured.

The composition may be in a fluid form.

The composition may be in the form of an oily gel or an emulsion.

The composition may be in a solid form.

According to the invention, the term "composition in solid form" means a composition which has a hardness such that it does not flow under its own weight, as opposed to "fluid" compositions. Such a composition may especially be in the form of a compact powder or in the form of a cast product.

The composition may be in emulsion form, in particular in the form of an oil-in-water or water-in-oil emulsion. The composition may be anhydrous. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

The composition may be a makeup and/or care composition.

The composition may be chosen from certain makeup compositions such as foundations, eyeshadows, face powders, lip glosses or lipsticks.

The composition may be chosen from skincare and lipcare compositions.

The oil present in the composition may be chosen from volatile and non-volatile oils of hydrocarbon-based, silicone or fluoro type. Preferably, the oil is a non-volatile oil.

The term "non-volatile oil" means an oil that remains on the skin at room temperature and atmospheric pressure for at least several hours, and that especially has a vapour pressure of less than 1.33 Pa (0.01 mmHg).

The term "hydrocarbon-based oil" means an oil mainly containing hydrogen and carbon atoms and optionally oxygen or nitrogen atoms.

Non-volatile hydrocarbon-based oils that may especially be mentioned include:
- hydrocarbon-based oils of animal origin,
- hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else capryllic/capric acid triglycerides, for instance those sold by the company Stéarineries Dubois or those sold under the names Miglyol 810®, 812® and 818® by the company Dynamit Nobel,
- synthetic ethers containing from 10 to 40 carbon atoms;
- linear or branched hydrocarbons of mineral or synthetic origin, such as petroleum jelly, polydecenes, hydrogenated polyisobutene such as Parleam®, squalane and liquid paraffins, and mixtures thereof,
- synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters;
- fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol;
- higher fatty acids such as oleic acid, linoleic acid or linolenic acid, and mixtures thereof.

The non-volatile silicone oils that may be used in the composition according to the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and mixtures thereof.

For the purposes of the invention, the term "volatile oil" means any oil that is capable of evaporating on contact with the skin, at room temperature and atmospheric pressure. The volatile oils of the invention are volatile cosmetic oils, which are liquid at room temperature, having a nonzero vapour pressure, at room temperature and atmospheric pressure, ranging in particular from 0.13 Pa to 40 000 Pa (0.001 to 300 mmHg) and preferably ranging from 1.3 Pa to 1300 Pa (0.01 to 10 mmHg).

The volatile hydrocarbon-based oils may be chosen from hydrocarbon-based oils containing from 8 to 16 carbon atoms, and especially branched $C_8$-$C_{16}$ alkanes such as $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, especially those with a viscosity ≤5 centistokes ($5 \times 10^{-6}$ m$^2$/s), and especially containing from 2 to 10 silicon atoms and preferably from 2 to 7 silicon atoms, these silicones optionally comprising alkyl or alkoxy groups containing from 1 to 10 carbon atoms. As volatile silicone oil that may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The oil may be present in the composition in a content ranging from 5% to 95% by weight and preferably ranging from 10% to 80% by weight relative to the total weight of the composition.

The composition may comprise water, especially in a mass content ranging from 5% to 90% and preferably ranging from 20% to 80% relative to the total mass of the composition.

Depending on the area of the keratin materials to be made up, the area of the body or the types of skin, one or the other effect, the transfer effect or the smoothing effect, is more particularly sought.

For example, in the case of skin that is naturally very smooth, a base coating that is particularly capable of promoting the transfer of the ink and of improving the visual appearance of the rendering is chosen, and in the case of skin bearing marks, it is above all the smoothing of the skin and good transfer of the ink that is sought.

The composition may also comprise conventional cosmetic additives chosen from film-forming polymers, waxes, pasty compounds, thickeners, surfactants, fragrances, preserving agents, sunscreens, fillers, dyestuffs, proteins, vitamins, provitamins, moisturizers, ceramides, pH regulators, and any other additive conventionally used in cosmetic compositions intended to be applied to keratin materials.

Printing

The term "digital printer" means a machine for printing in the form of pixels using digital data, different from a machine comprising a printing form. The printer may be an inkjet printer, for example a thermal or piezoelectric printer, a sublimation printer or a laser printer.

In one example, the printer is a laser printer arranged to allow the formation by electrophotography or magnetophotography of a coat of ink having a pattern on a transfer surface using at least one cosmetic toner and to deliver the toner present on the transfer surface in a state that is sufficiently free to allow it to be taken up or transferred by contact with the human keratin materials.

The term "cosmetic toner" should be understood as meaning a pulverulent cosmetic composition that is compatible with the formation of an image via an electrophotographic or magnetophotographic process as used in laser printers. Preferably, it is a toner that is suitable for electrophotographic use.

The toner is cosmetic in the sense that it is compatible with an application to human keratin materials. Depending on the surface to be made up, the formulation of the toner may be different. For example, for an application to the hair or the nails, it is possible to use certain compounds that might not be used for an application to the lips, for example.

The printer may be a food-grade inkjet printer of the Gatocopy A426 machine type allowing printing onto non-flat objects.

Cosmetic Ink—Dyestuff

The dyestuff may comprise one or more dyes as described below.

The dyestuff may be present in the ink in a mass content ranging from 0.01% to 60%, preferably ranging from 0.1% to 40%, or even from 0.1% to 30% and preferentially ranging from 0.5% to 20%, relative to the total mass of the ink.

The colouring ink may comprise one or more dyestuffs chosen from water-soluble dyes, liposoluble dyes, pulverulent dyestuffs such as pigments, especially nacres, and glitter flakes, or alternatively colouring polymers.

The term "pigments" should be understood as meaning white or coloured, mineral or organic particles of any form, which are insoluble in the cosmetic medium, and which are intended to colour the cosmetic ink.

The term "nacres" should be understood as meaning iridescent particles of any form, in particular produced by certain molluscs in their shell, or else synthesized.

The pigments may be white, black or coloured, and mineral and/or organic. Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment and also nacreous pigments based on bismuth oxychloride.

Among the water-soluble dyes, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue.

The ink may comprise at least one water-soluble dye.

Among the liposoluble dyes, mention may be made of Sudan Red III (CITA: D&C Red 17), lutein, quinizarine green (CTFA: D&C Green 6), alizurol purple SS (CTFA: D&C Violet 2), Sudan Brown, D&C Yellow 11, D&C Orange 5, quinoline yellow, curcumin, and carotenoid derivatives such as lycopene, beta-carotene, bixin or capsanthin, and mixtures thereof. The colouring polymers are generally copolymers based on at least two different monomers, at least one of which is a monomeric organic dye. Such polymeric dyes are known to those skilled in the art.

Reference may be made, for example, to the following documents: U.S. Pat. Nos. 5,032,670; 4,999,418; 5,106,942; 5,030,708; 5,102,980; 5,043,376; 5,104,913; 5,281,659; 5,194,463; 4,804,719; WO 92/07913 or EP 1 048 282.

The printing may use several different inks, especially inks of different colours.

The printing may use at least three, especially at least four, five, six, seven, eight, nine, ten; eleven or twelve cosmetic inks of different colours.

The printing may use only colouring inks that produce primary colours. As a variant, the printing uses both colouring inks that produce primary colours and at least one ink that produces a non-primary colour.

In one variant, the printing may use colouring inks that produce black and/or white.

The printing of the ink may be three-colour or four-colour printing.

The pattern obtained by printing may comprise several areas of different colours. As a variant, the pattern obtained by printing is a flat tint.

The pattern formed by the cosmetic ink printed on the transfer surface may be of any type.

The pattern may reproduce the appearance of relief and/or colour heterogeneities of the skin, for example freckles or a mole.

The pattern formed by the colouring ink borne by the transfer surface may be coloured when observed under white light in the visible region (400 nm-800 nm). As a variant, the pattern is colourless under white light in the visible region, but may appear coloured when submitted to a chemical and/or energy stimulus, such as exposure to UV (365 nm-400 nm), for example when the colouring ink contains a photochromic or fluorescent dyestuff.

The colouring ink obtained by printing may be deposited in the form of raster spots and/or of raster lines, so as to form a halftone image, for example a monochromatic or polychromatic image.

The pattern formed by the colouring ink printed on the transfer surface may be of any type.

The pattern may reproduce the appearance of relief and/or colour heterogeneities of the skin, for example freckles or a mole.

The colouring ink may be liquid at the time of printing and may have, for example, a viscosity ranging from 1 mPa·s to 500 mPa·s and preferably from 1 mPa·s to 300 mPa·s at 25° C.

The viscosity of an ink of the invention may be measured according to any process known to those skilled in the art, and especially according to the following conventional process. At 25° C. using a Rheomat 180 viscometer, equipped with a spindle rotating at 200 rpm, a person skilled in the art can select the spindle for measuring the viscosity from the spindles M1, M2, M3 and M4 on the basis of his general knowledge, so as to be able to perform the measurement.

Advantageously, the colouring ink is not entirely dry on the substrate when it is applied to the keratin materials. The colouring ink may be in fluid form when it is applied to the keratin materials.

The colouring ink may be in emulsion form.

The ink may be pulverulent at the time of printing.

When the ink is in the form of a cosmetic toner, this toner may comprise, besides a colouring agent, a compound for controlling the electrical charge, a particular additional filler, a lubricant, a wax and/or a binder.

Preferably, the particles of the toner have a mean size of between 1 and 16 µm. The toner comprises, for example, pigments with a particle size of between 1 and 10 µm.

All or part of the colouring ink borne by the transfer surface may be applied by transfer the keratin materials.

In one embodiment example, at least 25% by mass, especially 50%, especially 75% and especially substantially all of the coat of colouring ink initially present on the transfer surface is applied by transfer to the keratin materials.

In one embodiment example, the application of the colouring ink is performed by application with pressure of the transfer surface onto the keratin materials.

Substrate

In one embodiment example, the substrate used in the invention comprises at least one translucent or transparent area.

The translucent or transparent area allows a user to see through the substrate and thus to visualize more easily the surface to be made up and/or treated before transferring the cosmetic ink. The presence of a translucent or transparent area thus advantageously contributes towards facilitating the production of a precise makeup result on the keratin materials.

The translucent or transparent area of the substrate can be totally or partly superposed with the coat of cosmetic ink, and especially may overlap it.

The coat of cosmetic ink may be superposed in its entirety on the translucent or transparent area of the substrate. As a variant, only part of the coat of cosmetic ink is superposed on the transparent area of the substrate.

The substrate may be made of a transparent or translucent material. In this case, the translucent or transparent area extends over the entire surface of the substrate.

The substrate may comprise a material in sheet form, especially a transparent material.

The substrate is preferentially based on a non-absorbent material, for example a plastic film. The substrate is advantageously non-porous, at least on the face intended to receive the print.

The transfer surface may retain the cosmetic ink by capillary action.

The transfer surface may or may not be planar.

In one embodiment example, the substrate comprises an indication regarding the nature of the keratin materials intended to be made up with the cosmetic ink. This indication may be printed with the same ink or otherwise as that intended to be transferred.

The transfer surface of the substrate may be defined by all or part of: the outer surface of an applicator roller, the surface of an applicator pad, an element in sheet form, a patch, the surface of a porous foam, especially a sponge or a wipe, a coarse brush, a fine brush or a flocked tip.

The transfer surface is defined, for example, by all or part of the surface of a deformable sheet mounted on the surface of an applicator roller.

The transfer surface may be elastically deformable. Thus, in a first configuration, the transfer surface may be flat, and, in a second configuration, the transfer surface may be incurved, for example so as to take the shape of the keratin materials to be made up.

In one embodiment example, the transfer surface is detachable from a part of the substrate.

The substrate may be reusable.

In one embodiment example according to the invention, the process also comprises a step of finishing the makeup obtained on the keratin materials, for example so as to attenuate the demarcations between a made-up area and an area not made up. The finishing of the makeup obtained may comprise a step of spreading the colouring ink to produce shading-off, for example.

According to another aspect, a subject of the invention is a kit for performing the process according to the invention as described previously, comprising:
  a makeup device having a transfer surface and a coat of at least one cosmetic colouring ink borne by the transfer surface, obtained by printing using at least one digital printer,
  a cosmetic composition comprising at least one oil, the composition being contained in a packaging assembly.

The composition packaging assembly is, in a known manner, any packaging that is suitable for storing cosmetic compositions (especially a bottle, tube, spray bottle or aerosol bottle).

The kit may comprise one case for containing both the device and the composition.

DESCRIPTION OF THE FIGURES

The invention may be understood more clearly on reading the following description and on examining the attached drawing, in which:

FIG. 1 shows an example of a makeup device used in a process according to the invention, FIG. 2 is a section along II-II of the makeup device of FIG. 1, FIGS. 3 to 6 represent different steps of an example of a makeup process according to the invention, FIG. 7 shows an example of a transfer makeup result produced according to the invention, and FIG. 8 shows a kit according to the invention.

FIGS. 1 and 2 show a makeup device 1 comprising a substrate 2 whose front side defines a transfer surface 3. The device 1 may, as illustrated, have only one face defining the transfer surface 3, bearing a coat 4 of at least one cosmetic colouring ink according to the invention.

In one variant, not shown, two transfer surfaces 3 are defined by the two opposite faces of the substrate 2. In this case, these surfaces may bear coats of different cosmetic colouring inks, these coats possibly differing by their colour, the nature of the colouring inks borne and/or by the patterns formed.

In the device 1 illustrated in FIGS. 1 and 2, the coat of colouring ink 4 borne by the transfer surface 3 was deposited by printing using a digital printer, which deposits the ink dots in correspondence with the pixels of an image to be reproduced, for example in the form of rasters.

The coat of colouring ink 4 may form any type of pattern, for example in the form of two butterflies as illustrated.

Preferably, the substrate 2 has at least one non-opaque area 5, which is preferably transparent or translucent, and which may totally or partly be superposed with the coat of colouring ink 4. The transparent area 5 allows the user to see through the substrate 2 and thus to visualize the surface to be made up through the device 1 when this device is superposed on the said surface.

All of the coat of ink 4 may, as illustrated, be superposed on the transparent area 5. In one variant, not shown, only part of the coat of ink is superposed on the transparent area 5.

The substrate 2 may be made of a transparent material. The transparent area 5 then extends over the entire surface of the substrate 2.

The substrate 2 may bear an indication 7, for example a print, which gives information regarding a recommended positioning for the makeup, or the nature of the keratin materials intended to be made up with the colouring ink 4, or the like, and may also provide information regarding the colour and/or pattern reference. Indication 7 illustrates, for example at a reduced scale, "fight side" on the deposited pattern and "wrong side" on the substrate 2.

The pattern may be monochromatic or, better still, polychromatic. In this case, the coat of ink 4 may comprise several cosmetic inks that are locally juxtaposed at the microscopic scale, depending on the colour to be reproduced. The resolution of the printed pattern defined by the coat 4 may be between 16 dpi and 1600 dpi.

The coat of ink 4 may comprise several successive deposits of ink at the same place, so as to increase the amount of ink deposited on the substrate. The density of cosmetic ink dry matter of the coat 4 ranges, for example, from 0.01 mg/cm$^2$ to 100 mg/cm$^2$, or even from 0.1 mg/cm$^2$ to 10 mg/cm$^2$, better still from 0.2 mg/cm$^2$ to 10 mg/cm$^2$, in particular from 0.2 mg/cm$^2$ to 5 mg/cm$^2$.

The substrate 2 is preferably made of a flexible material. As a variant, the substrate 2 is made of a rigid or semi-rigid material.

All or part of the area of the transfer surface 3 superposed on the coat 4 is preferably smooth and has a roughness of less than or equal to 1 mm, especially between 1 µm and 100 µm and preferably less than or equal to 50 µm. The roughness is measured using a roughness meter, the tip of which has a radius of curvature of 10 mm, and the force of which, applied to the material to be characterized, is 6 mN.

FIGS. 3 to 6 schematically show various steps of an example of a makeup process according to the invention for making up an area of keratin materials P, in this case the lips.

As shown in FIG. 3, prior to transferring the ink of the coat 4, the area P is covered with a base coating 6 to prepare the area P and to facilitate the transfer of the cosmetic ink. In this example, the coating 6 is colourless.

Next, as illustrated in FIG. 4, the device 1 is brought close to the area P to be made up, so as to place the coat of colouring ink 4 in contact with the area P to be made up, and the user then applies a pressure allowing the ink 4 to be transferred onto the area P to be made up. During the contact with the keratin materials, the substrate 2 is preferably not moved sideways so as not to affect the appearance of the transferred pattern.

The pattern transferred onto the keratin materials corresponds to the pattern formed by the coat of colouring ink 4 when it is present on the substrate 2 (i.e. when it has not yet been transferred onto the keratin materials to be made up).

In one example, not shown, the process also comprises a step of finishing the makeup result obtained on the keratin materials.

FIG. 8 shows an embodiment example of a kit 30 for performing the process according to the invention. This kit comprises, in the same case, a plurality of devices 1 as described previously, each differing by the nature or form of the substrate 2 and/or by the pattern formed by the coat 4, especially its shape and/or its colour. The assembly also comprises a packaging assembly 50 containing a composition C comprising an oil, this composition being capable of forming a base coating 6 on the area P of the keratin materials to be made up.

The case may be leaktight so as to prevent the inks from drying out. The case may be made with means for preventing contact of the inks with a surface other than the transfer surface, so as to reduce the risk of premature transfer. For example, the case comprises a thermoformed shell whose wall extends at a distance from the areas of the substrate that are covered with inks.

EXAMPLES

Four inks corresponding to the formulations given in the table below were prepared:

|  | Yellow I | Magenta I | Cyan I | Black I |
|---|---|---|---|---|
| Dye | 1% | 1% | 1% | 1% |
| Isopropanol | 8% | 8% | 8% | 8% |
| Ethanol | 10% | 10% | 10% | 10% |
| Water | qs 100% | qs 100% | qs 100% | qs 100% |

These compositions are placed in Canon printer cartridges, and then used with a Canon Pixma IP100 inkjet printer, which is requested to print a makeup pattern produced with the PowerPoint® software, for example. The printing is performed on a transparent plastic sheet for a commercial printer (smooth side).

Example 1

In the Case of the Skin

This example corresponds to FIG. 7.

A single-colour pattern is produced by printing a coat of cosmetic ink 4 onto a substrate 2 in the form of a transparent plastic printer sheet using a digital printer.

This sheet is left for four days before use.

A coating 6 is produced on an area P of skin of an arm, with a foundation whose composition is described below.

| Foundation composition | |
|---|---|
| Ingredients | (weight %) |
| Magnesium sulfate | 1.50 |
| Distearyldimethylammonium-modified hectorite (Bentone 38 VCG from Elementis) | 1 |
| Titanium dioxide | 21.20 |
| Iron oxides | 3.8 |
| Sodium carboxymethylcellulose (Blanose ® 7M8SF from Ashland) | 0.50 |
| Cyclopentasiloxane | 15.30 |
| Polyglyceryl-4 isostearate cetyl PEG/PPG-10/1 hexyl laurate (Abil WE 09 from Evonik Goldschmidt) | 9 |
| Polydimethylsiloxane (viscosity: 5 cSt) (Xiameter PMX-200 Silicone Fluid 5 cs from Dow Corning) | 6.60 |
| Glycerol | 5 |
| Pentylene glycol | 3 |
| Water | qs 100 |

The plastic sheet covered with the coat of ink is then placed on the arm, and the plastic sheet is then removed.

Transfer of the pattern with partial integration onto the applied foundation is noted.

It is observed on the plastic sheet that the step of transferring the ink has not removed the foundation from the skin.

The same experiment is performed on the other arm, without prior application of foundation. No transfer is obtained.

Example 2

In the Case of the Lips

This example corresponds to FIGS. 1 to 6.

A makeup device 1 is produced by printing a coat 4 of cosmetic ink forming two butterfly-shaped multi-coloured patterns onto a transfer surface 3 of a plastic sheet.

| Lip gloss composition: | |
|---|---|
| Chemical name | (weight %) |
| Hydrophilic fumed silica (Aerosil 200 from Evonik Degussa) | 3.5 |
| Pigments | 0.3 |
| Castor oil | 14.6 |
| Beeswax | 2.7 |
| Polyester of hydrogenated castor oil and of dilinoleic acid dimer (Risocast DA-L from Kokyu Alcohol Kogyo) | 19.2 |
| Shea butter (Lipex Sheasoft from Aarhuskarlshamn) | 12 |
| Shea butter (Lipex Shea from Aarhuskarlshamn) | 12 |
| Fragrance | 0.4 |
| Hydrogenated polyester of dilinoleic acid and of butanediol (Viscoplast 14436 H from Biosynthis) | 35.3 |

A coating 6 is applied to the lips using a gloss having the composition described above, and the transfer surface is then placed on.

When the sheet is removed, it is observed that the two patterns are transferred onto the lips, with the colour and shape details corresponding to the starting patterns.

The expression "comprising a" should be understood as being synonymous with "comprising at least one".

The expression "between . . . and . . . " or "ranging from . . . to . . . " should be understood as including the limits.

The invention claimed is:

1. A process for making up an area of human keratin materials using a makeup device having a transfer surface, the process comprising:

printing by a digital printer a coat of at least one cosmetic colouring ink having a pattern on the transfer surface thereby forming a pattern borne by the transfer surface, the colouring ink is configured for application to the area of human keratin materials;

providing the makeup device having the transfer surface and the coat of at least one cosmetic colouring ink having the pattern borne by the transfer surface, forming a coloured base coating by applying at least one cosmetic composition comprising an oil onto the area of the human keratin materials to be made up, the cosmetic composition being a foundation or a lip gloss, producing the pattern on the area of the human keratin materials by placing the coat of cosmetic ink in contact with the base coating present on the area to be made up so as to transfer the coat of cosmetic ink onto the human keratin materials, the pattern only partially covering the base coating, moving the transfer surface away from the area of the human keratin materials after the coat of ink has been transferred, the transfer surface comprising a non-absorbent material so that the coloured base coating is not removed from the human keratin materials while transferring the coat of cosmetic ink having the pattern onto the human keratin materials and/or while moving the transfer surface away from the area of the human keratin materials, the ink being a pulverulent at the time of printing.

2. The process according to claim 1, the cosmetic composition being anhydrous or comprising an emulsion.

3. The process according to claim 1, the cosmetic composition comprising the oil in an amount by mass ranging from 5% to 95% relative to the total mass of the composition.

4. The process according to claim 1, the cosmetic composition also comprising at least one cosmetic additive chosen from film-forming polymers, waxes, pasty compounds, thickeners, surfactants, fragrances, preserving agents, sunscreens, fillers, dyestuffs, proteins, vitamins, provitamins, moisturizers, ceramides and pH regulators.

5. The process according to claim 1, the ink(s) being deposited onto the transfer surface without being covered and without covering a coat of an adhesive.

6. The process according to claim 1, the oil being a non-volatile oil.

7. The process according to claim 1, the ink comprising at least one water-soluble dye.

8. The process according to claim 1, wherein the ink is a solid pulverulent at the time of digital printing.

\* \* \* \* \*